United States Patent [19]

Cohen

[11] Patent Number: 5,056,197

[45] Date of Patent: Oct. 15, 1991

[54] CLIP OF EXTRUDED PLASTIC MATERIAL

[76] Inventor: Joel Cohen, 1020 NW. 99th Ave., Plantation, Fla. 33322

[21] Appl. No.: 660,723

[22] Filed: Feb. 25, 1991

[51] Int. Cl.⁵ .......................... A44B 21/00; A61B 5/04
[52] U.S. Cl. .......................................... 24/304; 24/543; 128/640; 128/641
[58] Field of Search ................. 24/304, 487, 489, 498, 24/513, 517, 543; 128/640, 641

[56] References Cited

U.S. PATENT DOCUMENTS

| | | | |
|---|---|---|---|
| 3,309,052 | 3/1967 | Borisof | 24/304 |
| 3,713,622 | 1/1973 | Dinger | 24/543 |
| 4,209,020 | 6/1980 | Nielsen | 128/641 |
| 4,332,257 | 6/1982 | Ayer | 128/641 |
| 4,382,453 | 5/1983 | Bujan et al. | 24/543 |
| 4,815,964 | 3/1989 | Cohen et al. | 128/641 |

*Primary Examiner*—Victor N. Sakran
*Attorney, Agent, or Firm*—Malloy, Downey & Malloy

[57] ABSTRACT

A clip of extruded plastic material especially useful for embracing and holding an electrode lead wire of an electrode in a predetermined position; the clip is composed of two hingedly connected leaf portions with mating hook portions to hold the clip leafs closed and wherein one of the leaf portions is configured with a lift tab portion for opening the clip to release the electrode lead wire; one of the leafs is provided with an adhesive surface to attach it to a support surface.

7 Claims, 1 Drawing Sheet

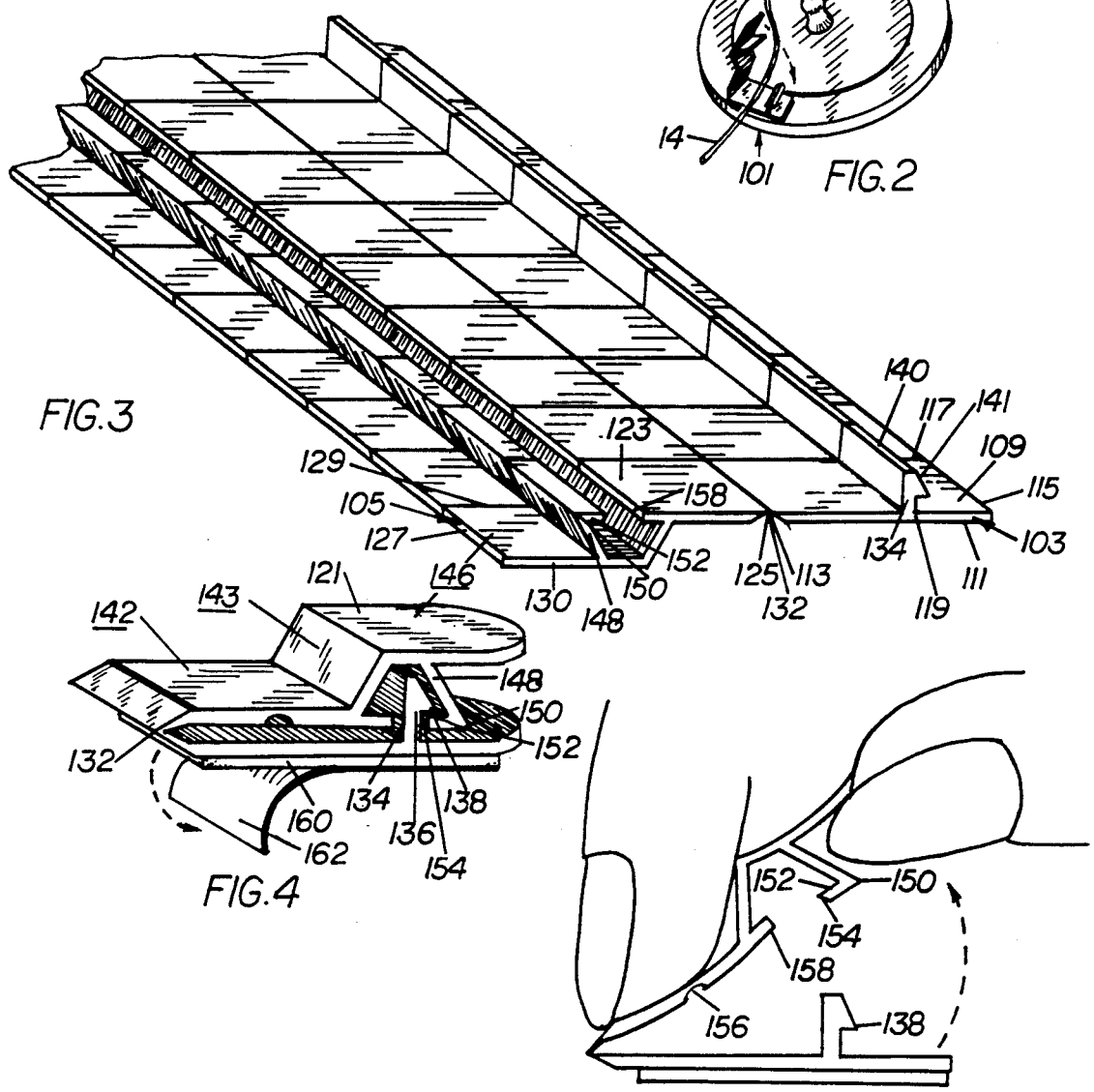

CLIP OF EXTRUDED PLASTIC MATERIAL

FIELD OF THE INVENTION

This invention relates to clips and to an extruded plastic clip which is especially useful when mounted to an electrode to hold a lead wire.

BACKGROUND OF THE INVENTION

As set forth in my earlier issued patent, U.S. Pat. No. 4,815,964, electrodes are often releasably attached to a person to learn about bodily functions, such as in an electrocardiogram procedure. Such electrodes often include an electrically conductive attachment post for electrical connection with a socket in a head with a lead wire extending from the head. In use, there is often a problem maintaining the head and post in electrical engagement. For example, when conducting a stress test, a patient is required to work or run on a treadmill and the attendant movement often causes the electrode heads and wires to become detached from the electrode post. Various patents have been issued, such as U.S. Pat. No. 4,332,257 to protect against the lead wire and head becoming disconnected from the electrode post. My earlier granted patent is of such a device and in one embodiment, FIG. 5 of my earlier patent, a clip is provided on the circumferential zone of the electrode to grasp the lead wire, which helps to maintain the required electrical connection. This invention is of an improved clip which is especially useful in combination with an electrode for the purposes set forth, namely guarding against disconnection of the lead wire and head from the electrode proper. The clip is, however, useful for grasping other items.

An important feature of this invention is that the clip is configured and structured such that it can be severed from an extruded plastic length. It is thus inexpensive, indeed disposable clip. If desired adhesive is applied to one of its surfaces so that it can be mounted on an electrode or the other support surface.

OBJECTS OF THE INVENTION

It is accordingly an object of the invention to provide a clip severed from a length of extruded plastic material which is composed of a pair of hingedly connected leafs and means on the leafs to hold the leafs releasably together in clasping and holding relation of an item captivated between the leafs. The clips are inexpensive and easily and rapidly produced in quantity.

DESCRIPTION OF THE DRAWINGS

FIG. 1 is a prior art electrode shown in cross section.

FIG. 2 is a perspective view of a lead wire and head, an electrode with a electrically conductive post and the clip of the present invention adhesively mounted on the electrode for holding the lead wire.

FIG. 3 is a perspective view of an extruded plastic length from which clips may be severed.

FIG. 4 is a perspective view of the clip.

FIG. 5 is a perspective view illustrating the operation of the clip in use upon being opened.

DESCRIPTION OF THE PREFERRED EMBODIMENT

Referring to the drawings, there is shown an electrode 12 having a protruding centrally arranged electrically conductive post 22 and an outer circular or circumferential zone 44. Shown in FIG. 2 is a lead wire 14 provided with a head 15 for electrical connection over the post 22. Attached to the electrode is a clip 101 in accordance with this invention which grasps the lead wire 14 to stabilize it and help to maintain the electrical connection of the lead wire head and post when in use. Referring now to the clip, it is configured to adapt it to be severed from an extruded plastic length, see FIG. 3. It is composed of two hingedly connected leafs, a base leaf 103 and a swing leaf 105 which are hingedly joined together. These leafs include means to hold the leafs releasably in clasping and holding relation of the lead wire or other item captivated between the leafs. To this end, the base leaf which is of a predetermined thickness, has an upper surface 109 and a flat outer surface 111. It also is configured with a straight hinge edge 113 and an outer edge 115 spaced from the hinge edge. Side edges 117 and 119 extend from the straight hinge edge to the outer edge. The swing leaf 105 is sized to overlay the upper surface of the base leaf and it has an exterior surface 121 and an inner surface 123. The inner surface 123 on swinging movement is hingedly moved into confronting relation to the upper surface 109 of the base leaf. This is its position when clamping and holding an item. The swing leaf 105 also has a straight hinge edge 125, as well as an outer edge 127 spaced from the straight hinge edge. Further it has a pair of opposed side edges 129 and 130 extending from the swing leaf straight edge to the swing leaf outer edge. The base leaf and the swing leaf are tapered preferably along their straight edges defining a weakened hinge zone 132 which is recessed or of reduced thickness. This weakened hinge zone 132 extends across the clip and defines a hinge flap hingedly interconnecting the leafs at the straight edges. On the upper surface 109 of the base leaf spaced from and parallel to the straight hinge edge 113, an upstanding lock wall 134 or stud wall is provided. It is relatively thick compared to the base leaf and is located adjacent the base leaf outer edge 115. The lock wall 134, it is seen in FIG. 4, has a terminal end zone 136. This lock wall comprises an upstanding stub portion integral with and on the upper surface of the base leaf which extends completely across the clip between the side edges 117 and 119. Further, the lock wall has an enlarged terminal end zone of the lock wall. This provides a lock shoulder 138 at the juncture of the enlarged end zone and the upstanding portion of the lock wall. The lock shoulder thus defines a surface generally parallel to and in spaced relation from the upper surface of the base leaf which extends from the upstanding portion of the lock wall to a terminal edge 140. It also extends in parallel relation to the straight hinge edges 113 and 125 completely across the clip 101 between the side edges 117 and 119. A cam surface 141 is thus defined between the terminal edge 140 and the terminal end 136 which extends upwardly and away from the base leaf outer edge and the terminal end. This cam surface also extends completely across the clip between the base leaf side edges 117 and 119 and is generally parallel to the straight edges 113 and 125. There is thus defined what may be considered a hook means for mating engagement with a companion hook means on the swing leaf, now to be described.

The swing leaf 105, see FIG. 4, is composed of three portions, a first portion 142 which extends outwardly away from the straight edges, a second outwardly extending intermediate portion 143 extending outwardly from the inner portion, and a lift tab portion 146 extending outwardly of the intermediate portion. The swing leaf also includes a catch rail 148 which extends downwardly away from the swing leaf tab portion and hooks up with the lock shoulder when the clip is in a closed position, as shown in FIG. 4. To this end, the catch rail extends away from the swing leaf straight edge to a catch wall terminal tip. The catch wall terminal tip 150, see FIG. 5, is enlarged with respect to said catch rail so as to define a catch surface 152 extending from the catch wall toward the swing leaf straight edge. This catch surface 152 is generally parallel to the inner surface of the swing leaf 105 and once again extends across the clip between the swing leaf side edges 129 and 130 to a cam follower edge 154. The cam follower edge 154 and the cam surface 141 are spaced from the straight hinge edges companionantly for mating sliding engagement of one another on swinging movement of closing of the clip leafs into hooked up engagement with one another to embrace an item captivated between the leafs straight edges and lock wall.

In a preferred embodiment, adhesive may be provided on the exterior surface of the base leaf, the adhesive means being indicated by the numeral 160. Also a liner means 162 may be provided to releasably and protectively overlay the adhesive coating or adhesive means. The clip is thus adapted to be adhesively combined with an electrode with the clip being arranged adjacent the peripheral edge of the electrode, that is, in the circumferential zone 44. In a preferred embodiment, a groove or recess 156 is provided extending across the clip between the swing leaf side edges 129 and 130 between the straight hinge edges and the intermediate portion to nestle a wire positioned. Also in a preferred embodiment, the swing leaf may include a flange extending from the swing leaf first portion 142 toward the lift tab portion, this flange being generally indicated by the number 158.

In use, the adhesive is exposed by removing the liner and the base leaf is secured to a support surface such as the surface of an electrode. Thereafter, an item, such as a lead wire 14, may be positioned across the base leaf and the swing leaf hingedly moved into hooked up relation with the base leaf as shown in FIG. 4 to embrace the wire and captivate it. To provide for flexibility, the recess or groove may be provided in the swing leaf to assist in keeping the lead wire in position; however, this is not necessarily essential. The clips are inexpensive and merely severed from an extruded plastic length and they may be trimmed by stamping or the like to round the edges at the corners. In use, see FIG. 5, the lift tab portion is raised by the thumb while the index finger bears and applies pressure against the intermediate surface which causes the release of the hooked up portions so that the captivated item may be easily removed after swinging movement of the swing leaf lift tab as shown in FIG. 5.

While this invention has been shown in a practical and preferred embodiment, it is recognized that departures can be made which would be within the spirit and scope of the invention and, therefore, modifications and changes within the scope and spirit of this invention are meant to be encompassed by the claims set forth herein.

What is claimed is:

1. A clip 101 of extruded plastic material including a hingedly connected base leaf 103 and a swing leaf 105, and means to hold the leaves releasably in clasping and holding relation of an item 107 captivated between the leaves, A) said base leaf being of a predetermined thickness and having an upper surface 109 and a flat outer surface 111 and having a straight hinge edge 113, an outer edge 115 spaced from the straight hinge edge, and a pair of spaced parallel side edges 117 and 119 extending from said straight hinge edge to said outer edge, B) said swing leaf 105 being sized to overlay the upper surface, swing leaf having an exterior surface 121 and an inner surface 123 to be hingedly moved into confronting relation to the upper surface 109 when clamping and holding an item and said swing leaf 105 having a straight hinge edge 125, an outer edge 127 spaced from said straight hinge edge, and a pair of opposed side edges 129, 130 extending from said swing leaf straight edge to said swing leaf outer edge, C) said base leaf and said swing leaf being tapered along said straight edges defining a recessed weakened hinge zone 132 of reduced thickness across said clip and hingedly interconnecting said leaves at said straight edges, D) an upstanding lock wall 134 on said base leaf upper surface spaced from and parallel to said straight hinge edge 113 and adjacent the base leaf outer edge 115, said lock wall 134 having a terminal end 136 and comprising an upstanding portion integral with and on said upper surface and extending across the clip between the side 117, 119 edges of said base leaf 103, and said lock wall having an enlarged end zone at the terminal end, a) a lock shoulder 138 at the juncture of said enlarged end zone and upstanding portion, said lock shoulder having a surface generally parallel to and in spaced relation from said upper surface 109 extending from said upstanding portion to a terminal edge 140 and extending in parallel relation to said straight hinge edges 113, 125 and extending across the clip 101 between said side edges 117, 119, and b) an inclined cam surface 141 between the terminal edge 140 and terminal end 136 and extending upwardly and away from said base leaf outer edge and said terminal end, said cam surface extending across the clip between said base leaf side edges 117 and 119 and being parallel to said straight edges 113 and 125, E) said swing leaf 105 including a) a first portion 142 extending outwardly away from said straight edges, b) an outwardly extending intermediate portion 144 extending outwardly from said inner portion, and c) a left tab portion 146 extending outwardly of said intermediate portion, d) a catch rail 148 extending downwardly away from said swing leaf tab portion and away from said swing leaf straight edge to a catch wall terminal tip, said catch wall terminal tip 150 being enlarged with respect to said catch rail defining a catch surface 152 extending from the catch wall toward the swing leaf straight edge, e) said catch surface 152 being generally parallel to the inner surface of said swing leaf 105 and extending between the swing leaf side edges 129 and 130 to a cam follower edge, and F) said cam follower edge 154 and said cam surface 141 being spaced from said straight hinge edges components for mating sliding engagement of one another on swinging movement of closing of said clip leaves into hooked up engagement with one another to embrace an item between the leaves straight edges and lock wall, 2. A clip as set forth in claim 1 wherein said inner surface of said swing leaf first portion is provided with a recess 156 extending across the clip between the swing leaf side edges 129 and 130 and being located between said straight hinge edges and said intermediate portion to receive a wire thereon.

3. The clip as set forth in claim 1 wherein said first portion includes a flange 15B extending towards said cam follower edge and between said side edges 129 and 130.

4. The clip as set forth in claim 1 wherein adhesive means 160 are provided on the lower flat surface.

5. The clip as set forth in claim 4 wherein liner means 162 are provided releasably and protectively overlaying said adhesive coating.

6. The clip as set forth in claim 4 and in adhesive engagement with an electrode adjacent an electrode having a circumferential edge and said clip being adjacent said circumferential edge.

7. The clip as set forth in claim 1 wherein said side edges are rounded at said outer edges.

* * * * *